United States Patent
Sievernich et al.

[11] Patent Number: 6,103,664
[45] Date of Patent: Aug. 15, 2000

[54] SYNERGISTIC HERBICIDAL MIXTURES CONTAINING CYCLOHEXENONE OXIME ETHERS

[75] Inventors: Bernd Sievernich, Böhl-Iggelheim; Max Landes, Gönnheim, both of Germany; Charles Finley, Greenville, Miss.; Karl-Otto Westphalen, Speyer, Germany; Helmut Walter, Obrigheim, Germany; Ulf Misslitz, Neustadt, Germany

[73] Assignee: BASF Aktiengesellschaft, Ludwigshafen, Germany

[21] Appl. No.: 09/043,452

[22] PCT Filed: Sep. 12, 1996

[86] PCT No.: PCT/EP96/04000

§ 371 Date: Mar. 17, 1998

§ 102(e) Date: Mar. 17, 1998

[87] PCT Pub. No.: WO97/10710

PCT Pub. Date: Mar. 27, 1997

[30] Foreign Application Priority Data

Sep. 20, 1995 [DE] Germany .......................... 195 34 848

[51] Int. Cl.[7] .................................................. A01N 43/02
[52] U.S. Cl. .......................................................... 504/140
[58] Field of Search .............................. 514/204; 504/140

[56] References Cited

U.S. PATENT DOCUMENTS

| | | | |
|---|---|---|---|
| 3,950,420 | 4/1976 | Sawaki et al. | 260/563 |
| 4,011,256 | 3/1977 | Sawaki et al. | 260/468 |
| 4,249,937 | 2/1981 | Iwataki et al. | 71/97 |
| 4,666,510 | 5/1987 | Watson et al. | 71/103 |
| 4,834,908 | 5/1989 | Hazen et al. | 252/356 |
| 5,022,914 | 6/1991 | Kast et al. | 71/88 |
| 5,190,573 | 3/1993 | Misslitz et al. | 504/292 |
| 5,228,896 | 7/1993 | Misslitz et al. | 504/288 |
| 5,250,505 | 10/1993 | Kast et al. | 504/292 |
| 5,364,833 | 11/1994 | Kast et al. | 504/289 |
| 5,374,609 | 12/1994 | Kast et al. | 504/344 |
| 5,411,936 | 5/1995 | Kast et al. | 504/244 |
| 5,563,114 | 10/1996 | Meyer et al. | 504/288 |
| 5,574,000 | 11/1996 | Kast et al. | 504/292 |
| 5,597,776 | 1/1997 | Bratz et al. | 504/105 |

FOREIGN PATENT DOCUMENTS

93/04581   3/1993   WIPO .

OTHER PUBLICATIONS

The Agrochemial Handbook, 3r ED., The Royal Society of Chemistry.

Primary Examiner—Jose' G. Dees
Assistant Examiner—Alton Pryor
Attorney, Agent, or Firm—Keil & Weinkauf

[57] ABSTRACT

Herbicidal compositions containing a) at least one cyclohexenone oxime ether of the formula I

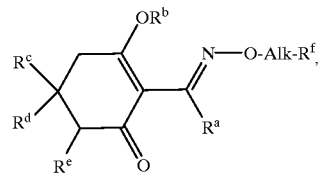

and b) at least one of the following 44 compounds:

b1) bromobutide, dimepiperate, etobenzanid, propanil,
b2) anilofos, mefenacet,
b3) 2,4-D, MCPB, naproanilide,
b4) bentazone,
b5) pyrazolynate/pyrazolate, sulcotrione,
b6) esprocarb, molinate, pyributicarb, thiobencarb/benthiocarb,
b7) quinclorac,
b8) butachlor, butenachlor, pretilachlor, thenylchlor,
b9) cycloxydim, sethoxydim,
b10) pendimethalin,
b11) cyhalofop-butyl, fenoxaprop-ethyl,
b12) benzofenap, pyrazoxyfen,
b13) dithiopyr,
b14) sodium 2,6-bis[(4,6-dimethoxypyrimidin-2-yl) oxy]-benzoate and methyl 2-[(4,6-dimethoxypyrimidin-2-yl)-oxy]-6-[1-(methoxyimino)ethyl]benzoate;
b15) azimsulfuron, bensulfuron-methyl, cinosulfuron, cyclosulfamuron, ethoxysulfuron, imazosulfuron, pyrazosulfuron-ethyl,
b16) dimethametryn, simetryn/simetryne,
b17) benfuresate,
b18) cafenstrole,
b19) cinmethylin,
b20) piperophos, are described.

10 Claims, No Drawings

SYNERGISTIC HERBICIDAL MIXTURES CONTAINING CYCLOHEXENONE OXIME ETHERS

This Application is a 371 of PCT/EP96/04000.

The present invention relates to novel herbicidal mixtures, containing a) at least one cyclohexenone oxime ether of the formula I

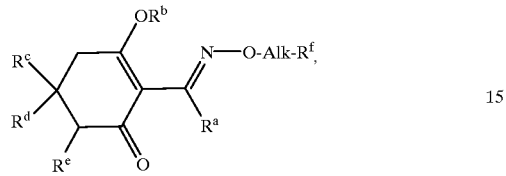

where the variables have the following meanings:

$R^a$ is a $C_1-C_6$-alkyl group;

$R^b$ is hydrogen, an equivalent of an agriculturally utilizable cation, a $C_1-C_6$-alkyl)carbonyl group, a $C_1-C_{10}$-alkylsulfonyl group, a $C_1-C_{10}$-alkylphosphonyl group or the benzoyl, benzenesulfonyl or benzenephosphonyl group, it being possible for the three last-mentioned groups, if desired, additionally to carry 1 to 5 halogen atoms;

$R^c$ is hydrogen, the cyano group, the formyl group, a $C_1-C_6$-alkyl group, a $C_1-C_4$-alkoxy-$C_1-C_6$-alkyl or $C_1-C_4$-alkylthio-$C_1-C_6$-alkyl group, a phenoxy-$C_1-C_6$-alkyl, phenylthio-$C_1-C_6$-alkyl, pyridyloxy-$C_1-C_6$-alkyl or pyridylthio-$C_1-C_6$-alkyl group, it being possible for all of the phenyl and pyridyl rings additionally to carry one to three radicals, in each case selected from the group consisting of nitro, cyano, halogen, $C_1-C_4$-alkyl, partially or completely halogenated $C_1-C_4$-alkyl, $C_1-C_4$-alkoxy, partially or completely halogenated $C_1-C_4$-alkoxy, $C_1-C_4$-alkylthio, $C_3-C_6$-alkenyl, $C_3-C_6$-alkenyloxy, $C_3-C_6$-alkynyl, $C_3-C_6$-alkynyloxy and —$NR^gR^h$, where $R^g$ is hydrogen, $C_1-C_4$-alkyl, $C_3-C_6$-alkenyl, $C_3-C_6$-alkynyl, $C_1-C_6$-acyl or benzoyl which can carry one to three radicals, in each case selected from the group consisting of nitro, cyano, halogen, $C_1-C_4$-alkyl, partially or completely halogenated $C_1-C_4$-alkyl, $C_1-C_4$-alkoxy and $C_1-C_4$-alkylthio and $R^h$ is hydrogen, $C_1-C_4$-alkyl, $C_3-C_6$-alkenyl or $C_3-C_6$-alkynyl;

a $C_3-C_7$-cycloalkyl or a $C_5-C_7$-cycloalkenyl group, it being possible for these groups additionally to carry one to three radicals, in each case selected from the group consisting of hydroxyl, halogen, $C_1-C_4$-alkyl, partially or completely halogenated $C_1-C_4$-alkyl, $C_1-C_4$-alkoxy, $C_1-C_4$-alkylthio, benzylthio, $C_1-C_4$-alkylsulfonyl and $C_1-C_4$-alkylsul-finyl, a 5-membered saturated heterocycle which contains one or two oxygen or sulfur atoms or one oxygen and one sulfur atom as hetero atoms, and which, if desired, can additionally carry one to three substituents, in each case selected from the group consisting of $C_1-C_4$-alkyl, partially or completely halogenated $C_1-C_4$-alkyl, $C_1-C_4$-alkoxy and $C_1-C_4$-alkylthio, a 6- or 7-membered saturated or mono- or diunsaturated heterocycle which contains one or two oxygen or sulfur atoms or one oxygen and one sulfur atom as hetero atoms, and which, if desired, can additionally carry one to three substituents, in each case selected from the group consisting of hydroxyl, halogen, $C_1-C_4$-alkyl, partially or completely halogenated $C_1-C_4$-alkyl, $C_1-C_4$-alkoxy and $C_1-C_4$-alkylthio, a 5-membered heteroaromatic, containing one to three hetero atoms selected from a group consisting of one or two nitrogen atoms and one oxygen or sulfur atom, it being possible for the heteroaromatic, if desired, additionally to carry one to three substituents, in each case selected from the group consisting of cyano, halogen, $C_1-C_4$-alkyl, partially or completely halogenated $C_1-C_4$-alkyl, $C_1-C_4$-alkoxy, partially or completely halogenated $C_1-C_4$-alkoxy, $C_1-C_4$-alkylthio, $C_2-C_6$-alkenyl, $C_2-C_6$-alkenyloxy, $C_3-C_6$-alkynyloxy and $C_1-C_4$-alkoxy-$C_1-C_4$-alkyl, phenyl or pyridyl which both, if desired, can carry one to three radicals, in each case selected from the group consisting of nitro, cyano, formyl, halogen, $C_1-C_4$-alkyl, partially or completely halogenated $C_1-C_4$-alkyl, $C_1-C_4$-alkoxy, partially or completely halogenated $C_1-C_4$-alkoxy, $C_1-C_4$-alkylthio, $C_3-C_6$-alkenyl, $C_3-C_6$-alkenyloxy, $C_3-C_6$-alkynyl, $C_3-C_6$-alkynyloxy and —$NR^kR^l$, where $R^k$ is hydrogen, $C_1-C_4$-alkyl, $C_3-C_6$-alkenyl or $C_3-C_6$-alkynyl and $R^l$ is hydrogen, $C_1-C_4$-alkyl, $C_3-C_6$-alkenyl, $C_3-C_6$-alkynyl, $C_1-C_6$-acyl or benzoyl which can additionally carry one to three substituents, in each case selected from the group consisting of nitro, cyano, halogen, $C_1-C_4$-alkyl, partially or completely halogenated $C_1-C_4$-alkyl, $C_1-C_4$-alkoxy and $C_1-C_4$-alkylthio, $R^d$ is hydrogen, the hydroxyl group or, if $R^c$ is a $C_1-C_6$-alkyl group, a $C_1-C_6$-alkyl group;

$R^e$ is hydrogen, halogen, the cyano group, a ($C_1-C_4$-alkoxy)-carbonyl group or a $C_1-C_4$-alkylketoxime group;

Alk is a $C_1-C_6$-alkylene, $C_3-C_6$-alkenylene or $C_3-C_6$-alkynylene chain which in each case can additionally carry one to three radicals selected from a group consisting of one to three $C_1-C_3$-alkyl substituents, one to three halogen atoms and a methylene substituent (=$CH_2$);

a 3- to 6-membered alkylene or 4- to 6-membered alkenylene chain which, if desired, can carry one to three $C_1-C_3$-alkyl substituents, and which besides methylene or methine units contains one of the following bridge members: oxygen, sulfur, —SO—, —$SO_2$— or —$N(R^i)$—, where $R^i$ is hydrogen, $C_1-C_4$-alkyl, $C_3-C_6$-alkenyl or $C_3-C_6$-alkynyl;

$R^f$ is the phenyl group, a halophenyl group or a dihalophenyl group, it being possible for all of the phenyl rings, if desired, additionally to carry one to three radicals, in each case selected from the group consisting of nitro, cyano, formyl, halogen, $C_1-C_4$-alkyl, partially or completely halogenated $C_1-C_4$-alkyl, $C_1-C_4$-alkoxy, partially or completely halogenated $C_1-C_4$-alkoxy, $C_3-C_6$-alkenyl, $C_3-C_6$-alkenyloxy, $C_3-C_6$-alkynyl, $C_3-C_6$-alkynyloxy and —NR—$^kR^l$, where $R^k$ is hydrogen, $C_1$–$C_4$-alkyl, $C_3$–$C_6$-alkenyl or $C_3$–$C_6$-alkynyl and $R^l$ is hydrogen, $C_1$–$C_4$-alkyl, $C_3$–$C_6$-alkenyl, $C_3$–$C_6$-alkynyl, $C_1$–$C_6$-acyl or benzoyl which can additionally carry one to three substituents, in each case selected from the group consisting of nitro, cyano, halogen, $C_1$–$C_4$-alkyl, partially or completely halogenated $C_1$–$C_4$-alkyl, $C_1$–$C_4$-alkoxy and $C_1$–$C_4$-alkylthio, and b) at least one of the following 44 herbicidal compounds from the groups b1) to b20):

b1) the amides
2-bromo-3,3-dimethyl-N-(1-methyl-1-phenylethyl)butyramide (common name: bromobutide),
S-(1-methyl-1-phenylethyl) 1-piperidinecarbothioate (common name: dimepiperate),
4-ethoxybenz-2',3'-dihydrochloroanilide (common name: etobenzanid) and
N-(3,4-dichlorophenyl)propanamide (common name: propanil);

b2) the anilides
S-[2-[(4-chlorophenyl)(1-methylethyl)amino]-2-oxo-ethyl] O,O-dimethyl phosphorodithioate (common name: anilofos) and
2-(1,3-benzothiazol-2-yloxy)-N-methylacetanilide (common name: mefenacet);

b3) the aryloxyalkanecarboxylic acids
(2,4-dichlorophenoxy)acetic acid (common name: 2,4-D),
4-(4-chloro-2-methylphenoxy)butanecarboxylic acid (common name: MCPB) and
2-(2-naphthyloxy)propionanilide (common name: naproanilide);

b4) 3-isopropyl-1H-2,1,3-benzothiadiazin-4-(3H)one 2,2-dioxide (common name: bentazone);

b5) the bleachers
4-(2,4-dichlorobenzoyl)-1,3-dimethylpyrazol-5-yltoluene-4-sulfonate (common name: pyrazolynate, pyrazolate) and 2-(2-chloro-4-mesylbenzoyl)cyclohexane-1,3-dione (common name: sulcotrione);

b6) the carbamates
S-benzyl 1,2-dimethylpropyl(ethyl)thiocarbamate (common name: esprocarb),
N-(ethylthiocarbonyl)azepane (common name: molinate),
O-3-tert-butylphenyl 6-methoxy-2-pyridyl(methyl)thiocarbamate (common name: pyributicarb) and
4-chlorobenzyl N,N-diethylthiocarbamate (common name: thiobencarb, benthiocarb);

b7) 3,7-dichloroquinoline-8-carboxylic acid (common name: quinclorac);

b8) the chloroacetanilides
N-(butoxymethyl)-2-chloro-N-(2,6-diethylphenyl)acetamide (common name: butachlor),
(Z)-N-but-2-enyloxymethyl-2-chloro-2',6'-diethylacetanilide (common name: butenachlor),
N-(2-propoxyethyl)-2-chloro-N-(2,6-diethylphenyl)acetamide (common name: pretilachlor) and
α-chloro-N-(3-methoxy-2-thienyl)methyl-2',6'-dimethylacetanilide (common name: thenylchlor);

b9) the cyclohexenones
2-[1-(ethoxyimino)butyl]-3-hydroxy-5-(tetrahydrothiopyran-3-yl)-2-cyclohexen-1-one (common name: cycloxydim) and
(E/Z)-2-[1-(ethoxyimino)butyl]-5-[2-(ethylthio)propyl]-3-hydroxycyclohex-2-enone (common name: sethoxydim);

b10) N-(1-ethylpropyl)-3,4-dimethyl-2,6-dinitrobenzenamine (common name: pendimethalin);

b11) the phenoxyphenoxypropionic acid esters
n-butyl (R)-2-[4-(4-cyano-2-fluorophenoxy)phenoxy]propionate (common name: cyhalofop-butyl) and
ethyl 2-[4-(6-chlorobenzoxazol-2-yloxy)phenoxy]propionate (common name: fenoxaprop-ethyl);

b12) the protoporphyrinogen IX oxidase inhibitors
2-[4-(2,4-dichloro-m-toluyl)-1,3-dimethylpyrazol-5-yloxy]-4'-methylacetophenone (common name: benzofenap) and
2-[4-(2,4-dichlorobenzoyl)-1,3-dimethylpyrazol-5-yloxy]acetophenone (common name: pyrazoxyfen);

b13) 3,5-bis(methylthiocarbonyl)-2-difluoromethyl-4-(2-methylpropyl)-6-trifluoromethylpyridine (common name: dithiopyr);

b14) the pyrimidyl ethers
sodium 2,6-bis[(4,6-dimethoxypyrimidin-2-yl)oxy]benzoate and
methyl 2-[(4,6-dimethoxypyrimidin-2-yl)oxy]-6-[1-(methoxyimino)ethyl]benzoate;

b15) the sulfonylureas
1-(4,6-dimethoxypyrimidin-2-yl)-3-[1-methyl-4-(2-methyl-2H-tetrazol-5-yl)pyrazol-5-ylsulfonyl]urea (common name: azimsulfuron),
methyl α-(4,6-dimethoxypyrimidin-2-ylcarbamoylsulfamoyl)-O-toluate (common name: bensulfuron-methyl), 1-(4,6-dimethoxy-1,3,5-triazin-2-yl)-3-[2-(2-methoxyethoxy)phenylsulfonyl]urea (common name: cinosulfuron),
1-{[2-(cyclopropylcarbonyl)phenyl]aminosulfonyl}-3-(4,6-dimethoxypyrimidin-2-yl)urea (common name: cyclosulfamuron),
[[(4,6-dimethoxy-2-pyrimidinyl)amino]carbonyl]-2-ethoxyphenyl sulfamic acid ester (common name: ethoxysulfuron),
N-(2-chloroimidazo[1,2-a]pyridin-3-ylsulfonyl)-N'-(4,6-dimethoxy-2-pyrimidyl)urea (common name: imazosulfuron) and
ethyl 5-(4,6-dimethoxypyrimidin-2-ylcarbamoylsulfamoyl)-1-methylpyrazole-4-carboxylate (common name: pyrazosulfuron-ethyl);

b16) the triazines
$N^2$-(1,2-dimethylpropyl)-$N^4$-ethyl-6-methylthio-1,3,5-triazine-2,4-diamine (common name: dimethametryn) and bis(ethylamino)-6-methylthio-1,3,5-triazine (common name: simetryn, simetryne);

b17) 2,3-dihydro-3,3-dimethyl-5-benzofuranyl ethanesulfonate (common name: benfuresate);

b18) 1-diethylcarbamoyl-3-(2,4,6-trimethylphenylsulfonyl)-1,2,4-triazole (common name: cafenstrole);

b19) (1RS,2SR,4SR)-1,4-epoxy-p-menth-2-yl 2-methylbenzyl ether (common name: cinmethylin), and b20) S-2-methylpiperidinocarbonylmethyl O,O-dipropyl phosphorodithioate (common name: piperophos).

The invention additionally relates to herbicidal compositions, containing at least one liquid and/or solid carrier, if desired at least one adjuvant, and a) a herbicidally active amount of at least one cyclohexenone oxime ether of the formula I and b) a synergistically active amount of at least one herbicidal compound from group b).

In addition, the invention relates to processes for preparing these compositions and methods of controlling undesired vegetation.

In the case of crop protection compositions, it is basically desirable to improve the specific action of an active compound and the safety of action. The herbicidally active cyclohexenone oxime ethers I are generally highly suitable for controlling monocotyledon weeds in crops.

It is an object of the present invention to increase the selective herbicidal action of the cyclohexenone oxime ethers I against undesired weeds.

We have found that this object is achieved by the synergistic mixtures defined at the outset. In addition, herbicidal compositions have been found which contain these mixtures, as well as processes for their preparation and methods of controlling undesired vegetation using the cyclohexenone oxime ethers I and the herbicidally active compounds of group b), it being insignificant whether the latter and the cyclohexenone oxime ethers I are formulated and applied together or separately and in which sequence the application is carried out in the case of separate application.

The mixtures according to the invention show a superadditive synergistic action; the tolerability of the individual compounds a) or b) is in general retained for specific crop plants.

The cyclohexenone oxime ethers of the formula I are disclosed, for example, in EP-A-368 227, DE-A 40 14 983, DE-A 40 14 984, U.S. Pat. No. 5,228,896, DE-A 40 14 986 and DE-A 40 14 988.

The herbicidally active compounds from group b) are described, for example, in

Herbizide (Herbicides), Hock, Fedtke, Schmidt, Georg Thieme Verlag, 1st Edition 1995 (see quinclorac p. 238, molinat p. 32, butachlor p. 32, pretilachlor p. 32, dithiopyr p. 32, mefenacet p. 32, fenoxapropethyl p. 216, dimepiperate p. 32, pyrazolate p. 146, pyrazoxyfen p. 146, bensulfuron-methyl p. 31, pyrazosulfuronethyl p. 31, cinosulfuron p. 31, benfuresate p. 233, bromobutide p. 243, dimethametryn p. 118, esprocarb p. 229, pyributicarb p. 32, cinmethylin p. 32, propanil p. 32, 2,4-D p. 30, bentazon p. 30, azimsulfuron p. 175), Agricultural Chemicals, Book II Herbicides, 1993 (see thiobencarb p. 85, benzofenap p. 221, napropanilid p. 49, piperophos p. 102, anilofos p. 241, imazosulfuron p. 150, etobenzanid p. 54, sulcotrione p. 268, sethoxydim p. 253, cycloxydim p. 222) or Short Review of Herbicides & PGRs 1991, Hodogaya Chemical (see butenachlor p. 52, thenylchlor p. 52, 3-(2-chlorophenylmethyl)-1-(1-methyl-1-phenylethyl) urea p. 90, pendimethalin p. 58).

Other compounds of group b) are described in the publication Brighton Crop Protection Conference—Weeds—1993 {see cyclosulfamuron, p. 41, methyl 2-[(4,6-dimethoxypyrimidin-2-yl)oxy]-6-[1-(methoxyimino)ethyl] benzoate p. 47, sodium 2,6-bis[4,6-dime-thoxypyrimidin-2-yl)oxy]benzoate p. 61}.

With respect to n-butyl (R)-2-[4-(4-cyano-2-fluorophenoxy)phenoxy]propionate, reference may be made to EP-A 0 302 203, and with respect to 1-diethylcarbamoyl-3-(2,4,6-trimethylphenylsulfonyl)-1,2,4-triazole to EP-A 0 332 133.

Suitable active compounds a) are both the pure enantiomers and the racemates or diastereomer mixtures of the cyclohexenone oxime ethers I.

Particularly preferred cyclohexenone oxime ethers of the formula I are those where the variables have the following meanings, namely alone or in combination in each case:

$R^a$ is the ethyl or n-propyl group;

$R^b$, $R^d$ and $R^e$ are each hydrogen;

$R^c$ is a 6- or 7-membered saturated or mono- or diunsaturated heterocycle which contains one or two oxygen or sulfur atoms or one oxygen and one sulfur atom as hetero atoms, and which, if desired, can carry one to three substituents, in each case selected from the group consisting of hydroxyl, halogen, $C_1$–$C_4$-alkyl, partially or completely halogenated $C_1$–$C_4$-alkyl, $C_1$–$C_4$-alkoxy and $C_1$–$C_4$-alkylthio;

Alk is a $C_1$–$C_6$-alkylene, $C_3$–$C_6$-alkenylene or $C_3$–$C_6$-alkynylene chain which in each case can additionally carry one to three radicals selected from a group consisting of one to three $C_1$–$C_3$-alkyl substituents, one to three halogen atoms and one methylene substituent ($=CH_2$);

a 3- to 6-membered alkylene or 4- to 6-membered alkenylene chain which, if desired, can carry one to three $C_1$–$C_3$-alkyl substituents, and which besides methylene or methine units contains one of the following bridge members: oxygen, sulfur, —SO—, —$SO_2$— or —N($R^i$)—, where $R^i$ is hydrogen, $C_1$–$C_4$-alkyl, $C_3$–$C_6$-alkenyl or $C_3$–$C_6$-alkynyl;

$R^f$ is the phenyl group, a halophenyl group or a dihalophenyl group, it being possible all of for the phenyl groups, if desired, additionally to carry one to three radicals, in each case selected from the group consisting of nitro, cyano, formyl, halogen, $C_1$–$C_4$-alkyl, partially or completely halogenated $C_1$–$C_4$-alkyl, $C_1$–$C_4$-alkoxy, partially or completely halogenated $C_1$–$C_4$-alkoxy, $C_3$–$C_6$-alkenyl, $C_3$–$C_6$-alkenyloxy, $C_3$–$C_6$-alkynyl, $C_3$–$C_6$-alkynyloxy and —$NR^kR^l$, where $R^k$ is hydrogen, $C_1$–$C_4$-alkyl, $C_3$–$C_6$-alkenyl or $C_3$–$C_6$-alkynyl and $R^l$ is hydrogen, $C_1$–$C_4$-alkyl, $C_3$–$C_6$-alkenyl, $C_3$–$C_6$-alkynyl, $C_1$–$C_6$-acyl or benzoyl which can additionally carry one to three substituents, in each case selected from the group consisting of nitro, cyano, halogen, $C_1$–$C_4$-alkyl, partially or completely halogenated $C_1$–$C_4$-alkyl, $C_1$–$C_4$-alkoxy and $C_1$–$C_4$-alkylthio.

To date, the cyclohexenone oxime ethers I of the following Table 1 have proven particularly advantageous:

TABLE 1

I {$R^b$, $R^d$, $R^e$ = H}

| No. | $R^a$ | $R^c$ | Alk | $R^f$ |
|---|---|---|---|---|
| 1 | $C_2H_5$ | Tetrahydro-thiopyran-3-yl | —$(CH_2)_2$—O— | 4-Cl-phenyl |
| 2 | n-$C_3H_7$ | Tetrahydro-thiopyran-3-yl | —$(CH_2)_2$—O— | 4-Cl-phenyl |
| 3 | $C_2H_5$ | Tetrahydro-pyran-3-yl | —$(CH_2)_2$—O— | 4-Cl-phenyl |

-continued $$\text{I } \{R^b, R^d, R^e = H\}^-,$$

(Structure: cyclohexenone with OH, $R^c$ substituent, and =N—O—Alk—$R^f$ group with $R^a$)

| No. | $R^a$ | $R^c$ | Alk | $R^f$ |
|---|---|---|---|---|
| 4 | n-$C_3H_7$ | Tetrahydro-pyran-3-yl | —$(CH_2)_2$—O— | 4-Cl-phenyl |
| 5 | $C_2H_5$ | Tetrahydro-thiopyran-3-yl | —$(CH_2)_2$—O— | 4-F-phenyl |
| 6 | n-$C_3H_7$ | Tetrahydro-thiopyran-3-yl | —$(CH_2)_2$—O— | 4-F-phenyl |
| 7 | $C_2H_5$ | Tetrahydro-pyran-3-yl | —$(CH_2)_2$—O— | 4-F-phenyl |
| 8 | n-$C_3H_7$ | Tetrahydro-pyran-3-yl | —$(CH_2)_2$—O— | 4-F-phenyl |
| 9 | $C_2H_5$ | Tetrahydro-thiopyran-4-yl | —$(CH_2)_2$—O— | 4-Cl-phenyl |
| 10 | n-$C_3H_7$ | Tetrahydro-thiopyran-4-yl | —$(CH_2)_2$—O— | 4-Cl-phenyl |
| 11 | $C_2H_5$ | Tetrahydro-pyran-4-yl | —$(CH_2)_2$—O— | 4-Cl-phenyl |
| 12 | n-$C_3H_7$ | Tetrahydro-pyran-4-yl | —$(CH_2)_2$—O— | 4-Cl-phenyl |
| 13 | $C_2H_5$ | Tetrahydro-thiopyran-4-yl | —$(CH_2)_2$—O— | 4-F-phenyl |
| 14 | n-$C_3H_7$ | Tetrahydro-thiopyran-4-yl | —$(CH_2)_2$—O— | 4-F-phenyl |
| 15 | $C_2H_5$ | Tetrahydro-pyran-4-yl | —$(CH_2)_2$—O— | 4-F-phenyl |
| 16 | n-$C_3H_7$ | Tetrahydro-pyran-4-yl | —$(CH_2)_2$—O— | 4-F-phenyl |
| 17 | $C_2H_5$ | Tetrahydro-thiopyran-3-yl | —$CH_2CH(CH_3)$—O— | 4-Cl-phenyl |
| 18 | n-$C_3H_7$ | Tetrahydro-thiopyran-3-yl | —$CH_2CH(CH_3)$—O— | 4-Cl-phenyl |
| 19 | $C_2H_5$ | Tetrahydro-pyran-3-yl | —$CH_2CH(CH_3)$—O— | 4-Cl-phenyl |
| 20 | n-$C_3H_7$ | Tetrahydro-pyran-3-yl | —$CH_2CH(CH_3)$—O— | 4-Cl-phenyl |
| 21 | $C_2H_5$ | Tetrahydro-thiopyran-3-yl | —$CH_2CH(CH_3)$—O— | 4-F-phenyl |
| 22 | n-$C_3H_7$ | Tetrahydro-thiopyran-3-yl | —$CH_2CH(CH_3)$—O— | 4-F-phenyl |
| 23 | $C_2H_5$ | Tetrahydro-pyran-3-yl | —$CH_2CH(CH_3)$—O— | 4-F-phenyl |
| 24 | n-$C_3H_7$ | Tetrahydro-pyran-3-yl | —$CH_2CH(CH_3)$—O— | 4-F-phenyl |
| 25 | $C_2H_5$ | Tetrahydro-thiopyran-4-yl | —$CH_2CH(CH_3)$—O— | 4-Cl-phenyl |
| 26 | n-$C_3H_7$ | Tetrahydro-thiopyran-3-yl | —$CH_2CH(CH_3)$—O— | 4-Cl-phenyl |
| 27 | $C_2H_5$ | Tetrahydro-pyran-4-yl | —$CH_2CH(CH_3)$—O— | 4-Cl-phenyl |
| 23 | n-$C_3H_7$ | Tetrahydro-pyran-4-yl | —$CH_2CH(CH_3)$—O— | 4-Cl-phenyl |
| 29 | $C_2H_5$ | Tetrahydro-thiopyran-4-yl | —$CH_2CH(CH_3)$—O— | 4-F-phenyl |
| 30 | n-$C_3H_7$ | Tetrahydro-thiopyran-4-yl | —$CH_2CH(CH_3)$—O— | 4-F-phenyl |
| 31 | $C_2H_5$ | Tetrahydro-pyran-4-yl | —$CH_2CH(CH_3)$—O— | 4-F-phenyl |
| 32 | n-$C_3H_7$ | Tetrahydro-pyran-4-yl | —$CH_2CH(CH_3)$—O— | 4-F-phenyl |

Among the herbicides of group b) the following 33 are particularly preferred:

b1) the amides
   2-bromo-3,3-dimethyl-N-(1-methyl-1-phenylethyl) butyramide (common name: bromobutide),
   S-(1-methyl-1-phenylethyl) 1-piperidinecarbothioate (common name: dimepiperate),
   4-ethoxybenz-2',3'-dihydrochloroanilide (common name: etobenzanid) and
   N-(3,4-dichlorophenyl)propanamide (common name: propanil);

b2) 2-(1,3-benzothiazol-2-yloxy)-N-methylacetanilide, (common name: mefenacet);

b3) the aryloxyalkanecarboxylic acids
   (2,4-dichlorophenoxy)acetic acid (common name: 2,4-D),
   4-(4-chloro-2-methylphenoxy)butanecarboxylic acid (common name: MCPB) and 2-(2-naphthyloxy) propionanilide (common name: naproanilide);

b4) 3-isopropyl-1H-2,1,3-benzothiadiazin-4-(3H)one 2,2-dioxide (common name: bentazone);

b5) the bleachers
   4-(2,4-dichlorobenzoyl)-1,3-dimethylpyrazol-5-yltoluene-4-sulfonate (common name: pyrazolynate, pyrazolate) and
   2-(2-chloro-4-mesylbenzoyl)cyclohexane-1,3-dione (common name: sulcotrione);

b6) the carbamates
   S-benzyl 1,2-dimethylpropyl(ethyl)thiocarbamate (common name: esprocarb),
   N-(ethylthiocarbonyl)azepane (common name: molinate) and
   4-chlorobenzyl N,N-diethylthiocarbamate (common name: thiobencarb);

b7) 3,7-dichloroquinoline-8-carboxylic acid (common name: quinclorac);

b8) the chloroacetanilides
   N-(butoxymethyl)-2-chloro-N-(2,6-diethylphenyl) acetamide (common name: butachlor),
   (Z)-N-but-2-enyloxymethyl-2-chloro-2',6'-diethylacetanilide (common name: butenachlor),
   N-(2-propoxyethyl)-2-chloro-N-(2,6-diethylphenyl) acetamide (common name: pretilachlor) and α-chloro-N-(3-methoxy-2-thienyl)methyl-2',6'-dimethylacetanilide (common name: thenylchlor);

b11) ethyl 2-[4-(6-chlorobenzoxazol-2-yloxy)phenoxy] propionate (common name: fenoxapropethyl);

b12) the protoporphyrinogen IX oxidase inhibitors
   2-[4-(2,4-dichloro-m-toluyl)-1,3-dimethylpyrazol-5-yloxy]-4'-methylacetophenone (common name: benzofenap) and
   2-[4-(2,4-dichlorobenzoyl)-1,3-dimethylpyrazol-5-yloxy]acetophenone (common name: pyrazoxyfen);

b13) 3,5-bis(methylthiocarbonyl)-2-difluoromethyl-4-(2-methylpropyl)-6-trifluoromethylpyridine (common name: dithiopyr);

b15) the sulfonylureas
   1-(4,6-dimethoxypyrimidin-2-yl)-3-[1-methyl-4-(2-methyl-2H-tetrazol-5-yl)pyrazol-5-ylsulfonyl]urea (common name: azimsulfuron),
   methyl α-(4,6-dimethoxypyrimidin-2-ylcarbamoylsulfamoyl)-O-toluate (common name: bensulfuron-methyl),
   1-(4,6-dimethoxy-1,3,5-triazin-2-yl)-3-[2-(2-methoxyethoxy)phenylsulfonyl]urea (common name: cinosulfuron),
   1-{[2-(cyclopropylcarbonyl)phenyl]aminosulfonyl}-3-(4,6-dimethoxypyrimidin-2-yl)urea (common name: cyclosulfamuron), N-(2-chloroimidazo[1,2-a] pyridin-3-ylsulfonyl)-N'-(4,6-di-methoxy-2-pyrimidyl)urea (common name: imazosulfuron) and
   ethyl 5-(4,6-dimethoxypyrimidin-2-ylcarbamoylsulfamoyl)-1-methylpyrazole-4-carboxylate (common name: pyrazosulfuronethyl);

b16) the triazines

N$^2$-(1,2-dimethylpropyl)-N$^4$-ethyl-6-methylthio-1,3,5-triazine-2,4-diamine (common name: dimethametryn) and bis(ethylamino)-6-methylthio-1,3,5-triazine (common name: simetryn, simetryne);

b19) (1RS,2SR,4SR)-1,4-epoxy-p-menth-2-yl 2-methylbenzyl ether (common name: cinmethylin), and b20) S-2-methylpiperidinocarbonylmethyl O,O-dipropyl phosphorodithioate (common name: piperophos).

The mixtures according to the invention, or in the case of separate application the components a) or b), can very effectively control broad-leafed weeds and grass weeds in the crops rice, wheats, corn, barley or millet without noticeably damaging the crop plants. This effect occurs especially at low application rates.

Taking into account the versatility of the application method, the compositions according to the invention can additionally be employed in a further number of crop plants to eliminate undesired plants. Suitable crops, for example, are the following:

*Allium cepa, Ananas comosus, Arachis hypogaea, Asparagus officinalis, Beta vulgaris* spec. *altissima, Beta vulagris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Ficus elastica, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum (N.rustica), Olea europaea, Oryza sativa, Phaseolus lunatus, Phaseolus vulgaris, Picea abies,* Pinus spec., *Pisum sativum, Prunus avium, Prunus persica, Pyrus communis, Ribes sylestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera, Zea mays.*

Moreover, the mixtures according to the invention can also be used in crops which have been made tolerant to the action of herbicides by breeding, including genetic engineering methods.

The application of the mixtures according to the invention or preparation thereof can take place pre-emergence or post-emergence. If the active compounds are less tolerable to certain crop plants, application techniques can be used in which the herbicidal compositions are sprayed with the aid of spray equipment such that the leaves of the sensitive crop plants are not affected if possible, while the active compounds reach the leaves of undesired plants growing under them or the uncovered soil surface (post-directed, lay-by).

The preparations of the mixtures are principally supplied to the plants by leaf spraying. In this case, the application can be carried out, for example, with water as a carrier by customary spray techniques using amounts of spray mixture from approximately 100 to 1000 1/ha. Application of the compositions in the low volume or ultra-low volume method is just as possible as their application in the form of granules.

The components a) (cyclohexenone oxime ether I) and b) can be applied to the leaves and shoots together or separately after the emergence of plants. Preferably, in this case the components a) and b) are applied at the same time. However, it is also possible to bring both components separately into the field.

In the ready-to-apply preparation, the components a) and b) can be present in suspended, emulsified or dissolved form together or formulated separately. The application forms here in this case depend entirely on the intended uses.

The compositions according to the invention can be applied by spraying, atomizing, dusting, broadcasting or watering, for example in the form of directly sprayable aqueous solutions, powders, suspensions, even high-percentage aqueous, oily or other suspensions, or dispersions, emulsions, oil dispersions, pastes, dusting compositions, broadcasting compositions or granules. The application forms depend on the intended uses; in each case, if possible, they should guarantee the finest dispersion of the active compounds according to the invention.

Suitable inert additives are mineral oil fractions of medium to high boiling point, such as kerosene or diesel oil, and also coal tar oils and oils of vegetable or animal origin, aliphatic, cyclic and aromatic hydrocarbons, eg. paraffin, tetrahydronaphthalene, alkylated naphthalenes or their derivatives, alkylated benzenes or their derivatives, methanol, ethanol, propanol, butanol, cyclohexanol, cyclohexanone or strongly polar solvents, such as N-methylpyrrolidone or water.

Aqueous application forms can be prepared from emulsion concentrates, suspensions, pastes, wettable powders or water-dispersible granules by addition of water. For the preparation of emulsions, pastes or oil dispersions, the substrates [sic], as such or dissolved in an oil or solvent, can be homogenized in water by means of wetting agents, adherents, dispersants or emulsifiers. However, concentrates consisting of active substance, wetting agent, adherent, dispersant or emulsifier and, possibly, solvent or oil can also be prepared which are suitable for dilution with water.

Suitable surface-active substances (adjuvants) are the alkali metal, alkaline earth metal and ammonium salts of aromatic sulfonic acids, eg. lignosulfonic, phenolsulfonic, naphthalenesulfonic and dibutylnaphthalenesulfonic acid, and also of fatty acids, alkyl- and alkylarylsulfonates, alkyl, lauryl ether and fatty alcohol sulfates, and also salts of sulfated hexa-, hepta- and octadecanols as well as of fatty alcohol glycol ethers, condensation products of sulfonated naphthalene and its derivatives formaldehyde, condensation products of naphthalene or of naphthalenesulfonic acids with phenol and formaldehyde, polyoxyethylene octylphenol [sic] ethers, ethoxylated isooctyl-, octyl- or nonylphenol, alkylphenyl or tributylphenyl polyglycol ethers, alkylaryl polyether alcohols, isotridecyl alcohol, fatty alcohol-ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, broadcasting compositions and dusting compositions can be prepared by mixing or joint grinding of the active substances with a solid carrier.

Granules, eg. coated, impregnated and homogeneous granules can be prepared by binding the active compounds to solid carriers. Solid carriers are mineral earths such as silicic acids, silica gels, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegetable products such as cereal flour, tree bark meal, wood meal and nutshell meal, cellulose powder or other solid carriers.

The ready-to-apply formulations in general contain from 0.001 to 98% by weight, preferably 0.01 to 95% by weight, of active compounds.

Generally, component a) (cyclohexenone oxime ether I) and component b) are applied here in proportions by weight such that the desired synergistic effect occurs. Preferably, the mixture ratios a):b) are from 1:0.1 to 1:40, in particular 1:0.2 to 1:30, particularly preferably 1:0.3 to 1:15.

The application rates of pure active compound mixture, ie. a) and b) without formulation auxiliary, depending on control target, time of year, target plants and stage of growth, are from 0.01 to 5 kg/ha, preferably 0.1 to 3.0 kg/ha of active substance (a.s.).

Additionally, it may be of use to apply the compositions according to the invention together, additionally mixed with other crop protection agents, for example with agents for controlling pests or phytopathogenic fungi or bacteria. Further of interest is the miscibility with mineral salt solutions, which are employed for eliminating nutritional and trace element deficiencies. Nonphytotoxic oils and oil concentrates can also be added.

USE EXAMPLES

The effect of various representatives of the herbicidal mixtures according to the invention, or combinations consisting of a) and b), on the growth of undesired plants and crop plants in comparison to the herbicidal active compound a) alone emerges from the following test results:

The application of the herbicide mixtures was carried out post-emergence (foliar treatment), the cyclohexenone oxime ethers I being applied as emulsion concentrates (EC) containing 100 or 200 g/l of active compound and the herbicides of the component b) in the formulation in which they are available as a commercial product.

The tests were carried out in the open on small plots of sandy loam (pH from 6.2 to 7.0) or sandy clay (pH from 5.0 to 6.7) as soil.

List of test plants:

| Botanical name | English/US name |
| --- | --- |
| Brachiaria plantaginea | marmeladegrass, Alexandergrass |
| Cyperus iria | flatsedge, rice |
| Ischaemum rugosum | winklegrass, saromaccagrass |

The weeds had different sizes and stages of development; the average height, depending on the growth form, was from 5 to 20 cm.

The compositions were applied together or in succession, either as a tank mix or as a finished formulation, namely in the form of emulsions, aqueous solutions or suspensions. The dispersing agent used was water (350 l/ha). Application was carried out with the aid of a mobile plot-spraying machine.

The test period extended over 3 to 8 weeks; the crops, however, were additionally observed at later times.

The damage due to the synergistic mixtures was assessed with the aid of a scale from 0% to 100% in comparison with untreated control plots. 0 here means no damage and 100 the complete destruction of plants.

The following examples show the action of the mixtures according to the invention without, however, excluding the possibility of further applications.

In these examples, the value E was calculated according to the method of S. R. Colby {cf. "Calculating synergistic and antagonistic responses of herbicide combinations", Weeds 15 (1967) p. 20 ff} which is to be expected with an only additive action of the individual active compounds:

$$E = X + Y - \frac{XY}{100}$$

X=percentage of the herbicidal action of component a) at an application rate $\alpha$ Y=percentage of the herbicidal action of component b) at an application rate $\beta$ E=expected action (in %) of a)+b) at an application rate $\alpha+\beta$ If the value observed is higher than the value E calculated according to Colby, a synergistic effect is present.

The mixtures of a) and b) according to the invention have a higher herbicidal action than would be expected according to Colby on the basis of the observed actions of the individual components in the case of application on their own.

The results of the tests are shown in the following Tables 2 to 4:

TABLE 2

Herbicidal action of cyclohexenone oxime ether No. 18 and basagran on *Cyperus iria* in the open; post-emergence application

| Application rate [kg/ha of a.s.] | | Damage | Expected |
| --- | --- | --- | --- |
| No. 18 | Basagran | [%] | value E |
| 0.1 | — | 13 | — |
| — | 1.12 | 45 | — |
| 0.1 | 1.12 | 99 | 52.15 |

TABLE 3

Herbicidal action of cyclohexenone oxime ether No. 18 and quinclorac on *Ischaemum rugosum* in the open; post-emergence application

| Application rate [kg/ha of a.s.] | | Damage | Expected |
| --- | --- | --- | --- |
| No. 18 | Quinclorac | [%] | value E |
| 0.15 | — | 92 | — |
| — | 0.375 | 3 | — |
| 0.15 | 0.375 | 99 | 92.24 |

TABLE 4

Herbicidal action of cyclohexenone oxime ether No. 18 and quinclorac on *Brachiaria plantaginea* in the open; post-emergence application

| Application rate [kg/ha of a.s.] | | Damage | Expected |
| --- | --- | --- | --- |
| No. 18 | Quinclorac | [%] | value E |
| 0.075 | — | 85 | — |
| — | 0.25 | 2 | — |
| 0.075 | 0.25 | 98 | 79 |

We claim:

1. A herbicidal composition comprising a) at least one cyclohexenone oxime ether of the formula I

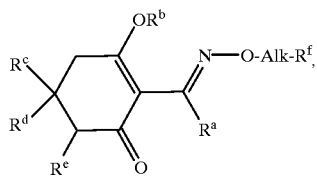

(I)

where the variables have the following meanings:
$R^a$ is ethyl or n-propyl;
$R^b$, $R^d$ and $R^e$ are each hydrogen;
$R^c$ is tetrahydropyran-3-yl, tetrahydropyran-4-yl or tetrahydrothiopyran-3-yl;
Alk is a chain —CH$_2$CH$_2$—O— or —CH$_2$CH(CH$_3$)—O—;
$R^f$ is 4-fluorophenyl or 4-chlorophenyl, and
b) at least one herbicidal compound selected from the groups $b_1$) to $b_{20}$)
$b_1$) the amines
2-bromo-3,3-dimethyl-N-(1-methyl-1-phenylethyl)-butyramide (common name: bromobutide),
S-(1-methyl-1-phenylethyl) 1-piperidinecarbothioate (common name: dimepiperate),
4-ethoxybenz-2',3'-dihydrochloroanilide (common name: etobenzanid) and
N-(3,4-dichlorophenyl)propanamide (common name: propanil);
$b_2$) the anilides
S-[2-[(4-chlorophenyl)(1-methylethyl)amino]-2-oxoethyl] O,O-dimethyl phosphorodithioate (common name: anilofos) and
2-(1,3-benzothiazol-2-yloxy)-N-methylacetanilide (common name: mefenacet);
$b_3$) the aryloxyalkanecarboxylic acids
(2,4-dichlorophenoxy)acetic acid (common name: 2,4-D),
4-(4-chloro-2-methylphenoxy)butanecarboxylic acid (common name: MCPB) and
2-(2-naphthyloxy)propionanilide (common name: naproanilide);
$b_4$) 3-isopropyl-1H-2,1,3-benzothiadiazin-4-(3H)one 2,2-dioxide (common name: bentazone);
$b_5$) the bleachers
4-(2,4-dichlorobenzoyl)-1,3-dimethylpyrazol-5-yltoluene-4-sulfonate (common name: pyrazolynate, pyrazolate) and
2-(2-chloro-4-mesylbenzoyl)cyclohexane-1,3-dione (common name: sulcotrione);
$b_6$) the carbamates
S-benzyl 1,2-dimethylpropyl(ethyl)thiocarbamate (common name: esprocarb),
N-(ethylthiocarbonyl)azepane (common name: molinate),
O-3-tert-butylphenyl 6-methoxy-2-pyridyl(methyl)thiocarbamate (common name: pyributicarb) and
4-chlorobenzyl N,N-diethylthiocarbamate (common name: thiobencarb, benthiocarb);
$b_7$) 3,7-dichloroquinoline-8-carboxylic acid (common name: quinchlorac);
$b_8$) the chloroacetanilides
N-(butoxymethyl)-2-chloro-N-(2,6-diethylphenyl)acetamide (common name: butachlor),
(Z)-N-but-2-enyloxymethyl-2-chloro-2',6'-diethylacetanilide (common name: butenachlor),
N-(2-propoxyethyl)-2-chloro-N-(2,6-diethylphenyl)acetamide (common name: pretilachlor) and
α-chloro-N-(3-methoxy-2-thienyl)methyl-2',6'-dimethylacetanilide (common name: thenylchlor);
$b_9$) the cyclohexenones
2-[1-(ethoxyimino)butyl]-3-hydroxy-5-(tetrahydrothiopyran-3-yl)-2-cyclohexen-1-one (common name: cycloxydim) and (E/Z)-2-[1-(ethoxyimino)butyl]-5-[2-(ethylthio)propyl]-3-hydroxycyclohex-2-enone (common name: sethoxydim);
$b_{10}$) N-(1-ethylpropyl)-3,4-dimethyl-2,6-dinitrobenzenamine (common name: pendimethalin);
$b_{11}$) the phenoxyphenoxypropionic acid esters
n-butyl (R)-2-[4-(4-cyano-2-fluorophenoxy)phenoxy]propionate (common name: cyhalofop-butyl) and
ethyl 2-[4-(6-chlorobenzoxazol-2-yloxy)phenoxy]propionate (common name: fenoxaprop-ethyl);
$b_{12}$) the protoporphyrinogen IX oxidase inhibitors
2-[4-(2,4-dichloro-m-toluyl)-1,3-dimethylpyrazol-5-yloxy]-4'-methylacetophenone (common name: benzofenap) and
2-[4-(2,4-dichlorobenzoyl)-1,3-dimethylpyrazol-5-yloxy]acetophenone (common name: pyrazoxyfen);
$b_{13}$) 3,5-bis(methylthiocarbonyl)-2-difluoromethyl-4-(2-methylpropyl)-6-trifluoromethylpyridine (common name: dithiopyr);
$b_{14}$) the pyrimidyl ethers
sodium 2,6-bis[(4,6-dimethoxypyrimidin-2-yl)oxy]benzoate and methyl 2-[(4,6-dimethoxypyrimidin-2-yl)oxy]-6-[1-(methoxyimino)ethyl]benzoate;
$b_{15}$) the sulfonylureas
1-(4,6-dimethoxypyrimidin-2-yl)-3-[1-methyl-4-(2-methyl-2H-tetrazol-5-yl)pyrazol-5-ylsulfonyl]urea (common name: azimsulfuron),
methyl α-(4,6-dimethoxypyrimidin-2-ylcarbamoylsulfamoyl)-O-toluate (common name: bensulfuron-methyl),
1-(4,6-dimethoxy-1,3,5-triazin-2-yl)-3-[2-(2-methoxyethoxy)phenylsulfonyl]urea (common name: cinosulfuron),
1-{[2-(cyclopropylcarbonyl)phenyl]aminosulfonyl}-3-(4,6-dimethoxypyridin-2-yl)urea (common name: cyclosulfamuron),
{[(4,6-dimethoxy-2-pyrimidinyl)amino]carbonyl}-2-ethoxyphenyl sulfamic acid ester (common name: ethoxysulfuron), N-(2-chloroimidazo[1,2-a]pyridin-3-ylsulfonyl)-N'-(4,6-dimethoxy-2-pyrimidyl)urea (common name: imazosulfuron) and ethyl 5-(4,6-dimethoxypyrimidin-2-ylcarbamoylsulfamoyl)-1-methylpyrazole-4-carboxylate (common name: pyrazosulfuron-ethyl);
$b_{16}$) the triazines
$N^2$-(1,2-dimethylpropyl)-$N^4$-ethyl-6-methylthio-1,3,5-triazine-2,4-diamine (common name: dimethametryn) and
bis(ethylamino)-6-methylthio-1,3,5-triazine (common name: simetryn, simetryne);
$b_{17}$) 2,3-dihydro-3,3-dimethyl-5-benzofuranyl ethanesulfonate (common name: benfuresate);
$b_{18}$) 1-diethylcarbamoyl-3-(2,4,6-trimethylphenylsulfonyl)-1,2,4-triazole (common name: cafenstrole);

$b_{19}$) (1RS,2SR,4SR)-1,4-epoxy-p-menth-2-yl 2-methylbenzyl ether (common name: cinmethylin), and $b_{20}$) S-2-methylpiperidinocarbonylmethyl O,O-dipropyl phosphorodithioate (common name: piperophos), in a synergistically effective amount where the cyclohexenone oxime ether and the herbicide from group b) in the weight ratio of from 1:0.1 to 1:40.

2. The synergistic herbicidal composition defined in claim 1, comprising at least one of the following 33 herbicides:

$b_1$) 2-bromo-3,3-dimethyl-N-(1-methyl-1-phenylethyl)-butyramide (common name: bromobutide),
S-(1-methyl-1-phenylethyl) 1-piperidinecarbothioate (common name: dimepiperate),
4-ethoxybenz-2',3'-dihydrochloroanilide (common name: etobenzanid) and
N-(3,4-dichlorophenyl)propanamide (common name: propanil);

$b_2$) 2-(1,3-benzothiazol-2-yloxy)-N-methylacetanilide (common name: mefenacet);

$b_3$) (2,4-dichlorophenoxy)acetic acid (common name: 2,4-D),
4-(4-chloro-2-methylphenoxy)butanecarboxylic acid (common name: MCPB) and
2-(2-naphthyloxy)propionanilide (common name: naproanilide);

$b_4$) 3-isopropyl-1H-2,1,3-benzothiadiazin-4-(3H)one 2,2-dioxide (common name: bentazone);

$b_5$) 4-(2,4-dichlorobenzoyl)-1,3-dimethylpyrazol-5-yltoluene-4-sulfonate (common name: pyrazolynate, pyrazolate) and 2-(2-chloro-4-mesylbenzoyl)cyclohexane-1,3-dione (common name: sulcotrione);

$b_6$) S-benzyl 1,2-dimethylpropyl(ethyl)thiocarbamate (common name: esprocarb),
N-(ethylthiocarbonyl)azepane (common name: molinate) and
4-chlorobenzyl N,N-diethylthiocarbamate (common name: thiobencarb);

$b_7$) 3,7-dichloroquinoline-8-carboxylic acid (common name: quinclorac);

$b_8$) N-(butoxymethyl)-2-chloro-N-(2,6-diethylphenyl)acetamide (common name: butachlor),
(Z)-N-but-2-enyloxymethyl-2-chloro-2',6'-diethylacetanilide (common name: butenachlor),
N-(2-propoxyethyl)-2-chloro-N-(2,6-diethylphenyl)acetamide (common name: pretilachlor) and
α-chloro-N-(3-methoxy-2-thienyl)methyl-2',6'-dimethylacetanilide (common name: thenylchlor);

$b_{11}$) ethyl 2-[4-(6-chlorobenzoxazol-2-yloxy)phenoxy]propionate (common name: fenoxaprop-ethyl);

$b_{12}$) 2-[4-(2,4-dichloro-m-toluyl)-1,3-dimethylpyrazol-5-yloxy]-4'-methylacetophenone (common name: benzofenap) and 2-[4-(2,4-dichlorobenzoyl)-1,3-dimethylpyrazol-5-yloxy]acetophenone (common name: pyrazoxyfen);

$b_{13}$) 3,5-bis(methylthiocarbonyl)-2-difluoromethyl-4-(2-methylpropyl)-6-trifluoromethylpyridine (common name: dithiopyr);

$b_{15}$) 1-(4,6-dimethoxypyrimidin-2-yl)-3-[1-methyl-4-(2-methyl-2H-tetrazol-5-yl)pyrazol-5-ylsulfonyl]urea (common name: azimsulfuron),
methyl α-(4,6-dimethoxypyrimidin-2-ylcarbamoylsulfamoyl)-O-toluate (common name: bensulfuron-methyl),
1-(4,6-dimethoxy-1,3,5-triazin-2-yl)-3-[2-(2-methoxyethoxy)phenylsulfonyl]urea (common name: cinosulfuron),
1-{[2-(cyclopropylcarbonyl)phenyl]aminosulfonyl}-3-(4,6-dimethoxypyridin-2-yl)urea (common name: cyclosulfamuron),
N-(2-chloroimidazol[1,2-a]pyridin-3-ylsulfonyl)-N'-(4,6-dimethoxy-2-pyrimidyl)urea (common name: imazosulfuron) and
ethyl 5-(4,6-dimethoxypyrimidin-2-ylcarbamoylsulfamoyl)-1-methylpyrazole-4-carboxylate (common name: pyrazosulfuroneethyl);

$b_{16}$) $N^2$-(1,2-dimethylpropyl)-$N^4$-ethyl-6-methylthio-1,3,5-triazine-2,4-diamine (common name: dimethametryn) and bis(ethylamino)-6-methylthio-1,3,5-triazine (common name: simetryn, simetryne);

$b_{19}$) (1RS,2SR,4SR)-1,4-epoxy-p-menth-2-yl 2-methylbenzyl ether (common name: cinmethylin), and $b_{20}$) S-2-methylpiperidinocarbonylmethyl O,O-dipropyl phosphorodithioate (common name: piperophos).

3. The synergistic herbicidal composition defined in claim 1, further comprising at least one liquid or solid carrier, and optionally at least one surface-active substance.

4. The synergistic herbicidal composition defined in claim 1, comprising the cyclohexenone oxime ether and the herbicide from group b) in the weight ratio of from 1:0.2 to 1:30.

5. The synergistic herbicidal composition defined in claim 3, comprising the cyclohexenone oxime ether and the herbicide from group b) in the weight ratio of from 1:0.1 to 1:40.

6. The synergistic herbicidal composition defined in claim 3, comprising the cyclohexenone oxime ether and the herbicide from group b) in the weight ratio of from 1:0.2 to 1:30.

7. A process for preparing the synergistic herbicidally active composition defined in claim 1, which comprises mixing
  a) a herbicidally active amount of at least one cyclohexenone oxime ether of the formula I and
  b) a synergistically active amount of at least one herbicidal compound from group b),
  with at least one inert liquid or and solid carrier and optionally at least one surface-active substance.

8. A method of controlling undesired vegetation, which comprises treating the vegetation with
  a) a herbicidally active amount of at least one cyclohexenone oxime ether of the formula I as defined in claim 1 and
  b) a synergistically active amount of at least one herbicidal compound from group b) as defined in claim 1,
  simultaneously or in succession before or during the emergence of the undesired plants.

9. A method of selectively controlling undesired vegetation, which comprises treating the leaves of the crop plants and of the undesired plants post-emergence with
  a) a herbicidally active amount of at least one cyclohexenone oxime ether of the formula I as defined in claim 1 and
  b) a synergistically active amount of at least one herbicidal compound from group b) as defined in claim 1.

10. The method of claim 9, wherein the crop plant is rice, wheat, corn, barley or millet.

* * * * *

UNITED STATES PATENT AND TRADEMARK OFFICE
CERTIFICATE OF CORRECTION

PATENT NO.: 6,103,664

DATED: August 15, 2000

INVENTOR(S): SIEVERNICH et al.

It is certified that error appears in the above-identified patent and that said Letters Patent is hereby corrected as shown below:

Col. 13, claim 1, line 21, "amines" should be --amides--.

Col. 13, claim 1, line 62, "quinchlorac" should be --quinclorac--.

Col. 14, claim 1, line 46, "(4,6-dimethyoxypyridin-2-yl)" should be --(4,6-dimethyoxypyrimidin-2-yl)- --.

Col. 15, claim 2, lines 33, 43, 47 and 51, insert a hyphen at the end of each line.

Col. 15, claim 2, line 42, "quinchlorac" should be --quinclorac--.

Col. 16, claim 2, line 5, "(4,6-dimethyoxypyridin-2-yl)urea" should be --(4,6-dimethyoxypyrimidin-2-yl)urea--.

Col. 16, claim 2, line 12, "pyrazosulfuroneethyl" should be --pyrazosulfuron-ethyl--.

UNITED STATES PATENT AND TRADEMARK OFFICE
CERTIFICATE OF CORRECTION

PATENT NO.: 6,103,664

DATED: August 15, 2000

INVENTOR(S): SIEVERNICH et al.

It is certified that error appears in the above-identified patent and that said Letters Patent is hereby corrected as shown below:

Col. 16, claim 2, line 7, "N-(2-chloroimidazol" should be --N-2(-chloroimidazo--.

Col. 16, claim 2, line 12, "pyrazosulfuroneethyl" should be --pyrazosulforunoethyl--.

Col. 16, claim 7, line 45, "or and" should be --or--.

Signed and Sealed this

Tenth Day of April, 2001

Attest:

NICHOLAS P. GODICI

Attesting Officer

Acting Director of the United States Patent and Trademark Office